US00PP33607P2

(12) United States Plant Patent
Hansen

(10) Patent No.: US PP33,607 P2
(45) Date of Patent: Nov. 2, 2021

(54) ***PHLOX* PLANT NAMED 'ULTRAVIOLET'**

(50) Latin Name: *Phlox paniculata*
Varietal Denomination: Ultraviolet

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/974,232

(22) Filed: Nov. 19, 2020

(51) Int. Cl.
*A01H 5/02* (2018.01)
*A01H 6/70* (2018.01)

(52) U.S. Cl.
USPC ..... Plt./320

(58) Field of Classification Search
USPC ..... Plt./320
CPC ... A01H 5/02; A01H 5/00; A01H 6/70; A01H 6/36
See application file for complete search history.

(56) References Cited

U.S. PATENT DOCUMENTS

PP19,813 P2 * 3/2009 Verschoor ..... A01H 5/02 Plt./320

* cited by examiner

*Primary Examiner* — June Hwu

(57) ABSTRACT

A unique cultivar of Tall *Phlox* named 'Ultraviolet' characterized by vigorous, tall, dense, upright, multi-stemmed, winter-hardy habit with dark-green, lanceolate leaves. Flowering on large heavily branched panicles begins in late-July and continues for up to five weeks completely covering the top of the plant in peak season. Petals are dark magenta-violet with a deep magenta eye. The new plant shows good powdery mildew resistance. The new plant is especially suitable for a cut flower, for the landscape as a potted plant and in the garden as a specimen or en masse.

2 Drawing Sheets

Botanical classification: *Phlox paniculata.*
Variety denomination: 'Ultraviolet'.

STATEMENT REGARDING PRIOR DISCLOSURES UNDER 37 CFR 1.77(b)(6)

The first non-enabling disclosure of the claimed plant, in the form of a photograph and brief description on a website operated by Walters Gardens, Inc. on Dec. 1, 2019. Subsequently, the new plant was advertised in the "Walters Gardens 20-21 Catalog" by Walters Gardens, Inc. released on May 20, 2020. The claimed plant was first sold to Ivy Acres, Inc. on Feb. 24, 2020 by Walters Gardens, Inc., who obtained the plant and all information relating thereto, from the inventor. No plants of *Phlox* 'Ultraviolet' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of Tall *Phlox* plant known as *Phlox* 'Ultraviolet' and will be referred to hereafter by its cultivar name, 'Ultraviolet', or the "new plant". The new plant was hybridized by the inventor at a wholesale perennial nursery in Zeeland, Mich. as a cross between *Phlox paniculata* 'Nicky' (sometimes referred to as 'Düsterlohe') (not patented) as the female or seed parent and *Phlox paniculata* 'Swirly Burly' (not patented) as the male or pollen on Aug. 8, 2013, with the seeds collected in the fall of 2013. The new plant passed initial evaluation in the summer of 2015 and was assigned the breeder code 13-212-1 through the remaining evaluation process. 'Ultraviolet' was first asexually propagated by division in the greenhouses at the same nursery in Zeeland, Mich. in the fall of 2015 followed by shoot tip cuttings in the summer of 2016. The unique characteristics of the new plant have been found to be reproducible and stable in successive generations of asexually propagated and the resultant plants have been found to be identical to the original selection.

BRIEF SUMMARY OF THE PLANT

*Phlox* 'Ultraviolet' is unique from all other Tall *Phlox* known to the inventor. The nearest comparison plants known to the inventor include: the female and male parents, 'Roberta' (not patented) and 'Tatjana' (not patented). 'Roberta' has flowers of slightly more reddish hue and the petals are coarsely sinuate. 'Tatjana' is more prone to powdery mildew infection and the flower center has a larger light-lavender to near-white eye. 'Nicky' has a shorter more open habit but the flowers are less violet-colored, while the new plant has darker stems, is more floriferous and has greater resistance to powdery mildew. The new plant also begins flowering about a week later than 'Nicky' with thicker stems. 'Swizzle' U.S. Plant Pat. No. 19,813 has a shorter habit and more pink flowers that fade to whiter petal faces. 'Swirly Burly' has a shorter habit with a pale lavender flower with a large darker eye of purplish-red.

*Phlox* 'Ultraviolet' differs from and all other *Phlox* known to the inventor in the following repeatedly observed traits in combination:

1. Vigorous plants of tall, dense, upright habit, producing clean, dark-green, lanceolate leaves;
2. Multiple stems produce large branched panicles;

3. Flowers beginning in late-July and continuing for up to five weeks completely covering top of plant at peak flowering;
4. Flowers of dark magenta-violet and deep magenta eye;
5. Good powdery mildew resistance.

BRIEF DESCRIPTION OF THE DRAWINGS

The photographs of the new plant demonstrate the unique traits of *Phlox* 'Ultraviolet' and the overall appearance of the plant at three-years-old growing in a full-sun trial garden in Zeeland, Mich. The colors in the drawings are as accurate as reasonably possible with color reproductions. Variation in ambient light spectrum, source and direction may cause the appearance of minor variation in color.

DETAILED BOTANICAL DESCRIPTION

Figure 1:
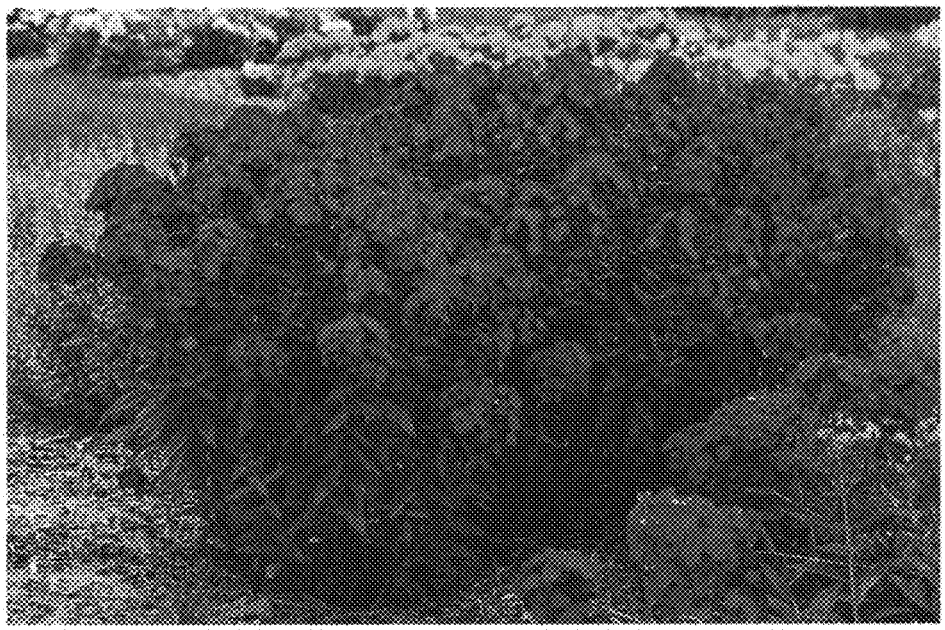
FIG. 1 shows a landscape habit view of the new plant in peak flower.
Figure 2:
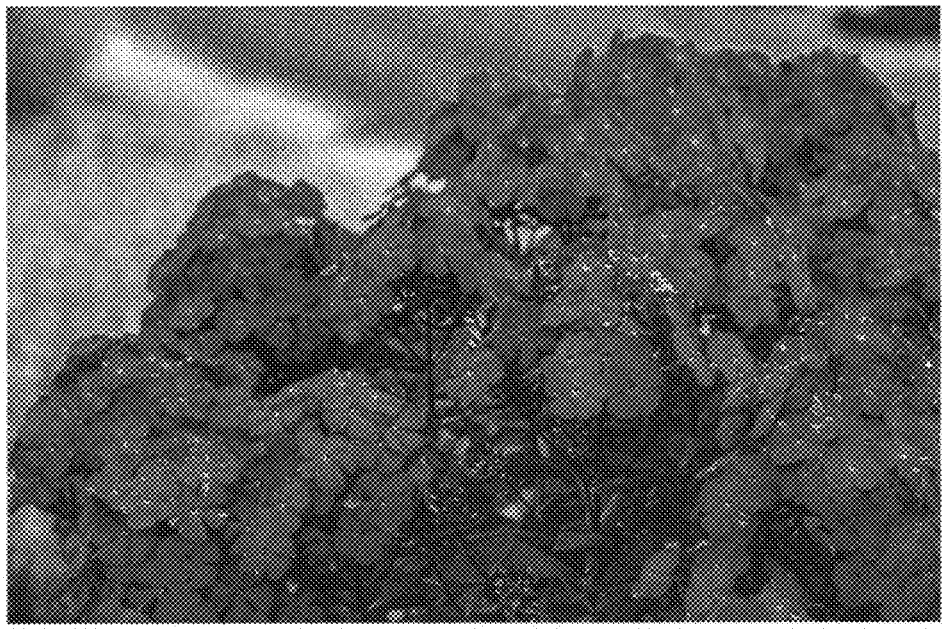
FIG. 2 shows a close-up of the flowers.
Figure 3:
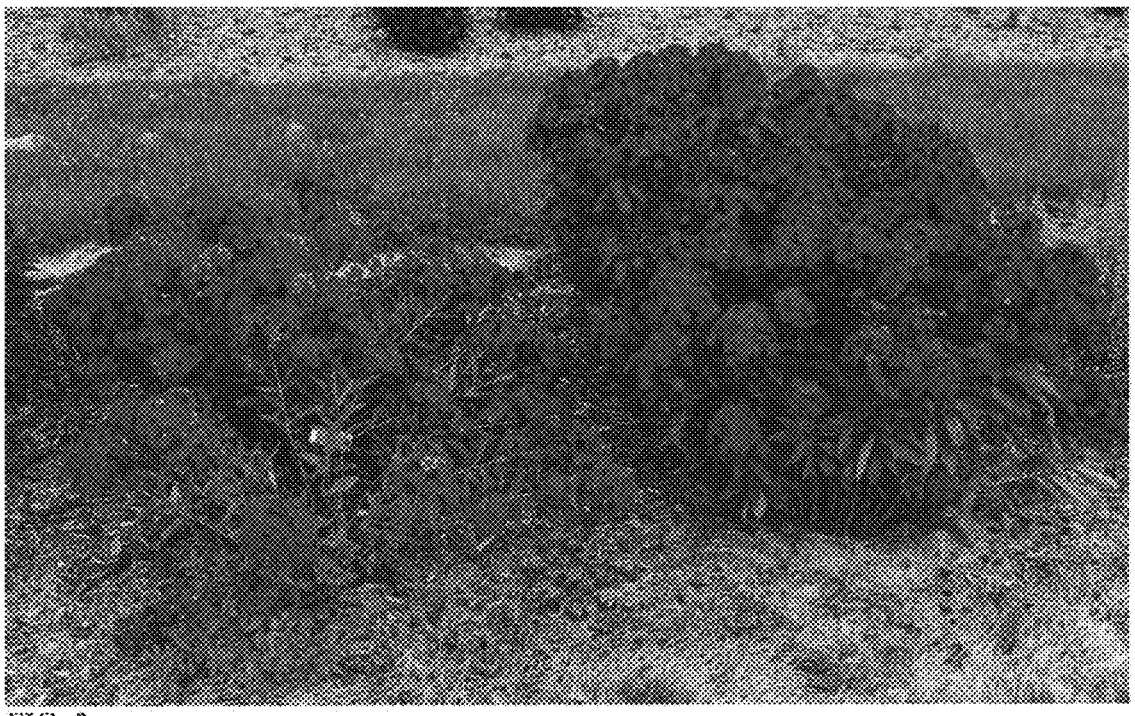
FIG. 3 shows a comparison with the new plant on the right and 'Nicky' on the left.

The following descriptions and color references are based on the 2015 edition of The Royal Horticultural Society Colour Chart except where common dictionary terms are used. *Phlox* 'Ultraviolet' has not been observed under all possible environments. The phenotype may vary slightly with different growing environments such as temperature, light, fertility, soil pH, moisture and maturity levels, but without any change in the genotype. The following observations and size descriptions are based on two-year-old plants in a partially shaded greenhouse or a full-sun trial garden of a wholesale perennial nursery in Zeeland, Mich. with supplemental fertilizer and water as needed.

Botanical classification: *Phlox* hybrid;

Parentage: Female or seed parent is 'Nicky'; the male or pollen parent is 'Swirly Burly';

Plant habit: Winter-hardy, herbaceous perennial; dense, producing up to about 29 stiff, upright stems; flowering to about 92.0 cm tall and 78.0 cm wide;

Propagation: Stem cuttings; rooting in about 3 weeks;

Time to produce finished crop in 3.8 liter pots: About 8 to 10 weeks; vigorous;

Root: Fibrous and freely branching; color creamy white to tan depending on soil type;

Leaves: Simple; opposite; lanceolate; apex narrowly acute; base attenuate, clasping; margin micro-ciliolate; glabrous both adaxial and abaxial; to about 16.0 cm long by about 4.8 cm wide, average about 14.2 cm long and 4.2 cm wide; anthocyanin pigment not observed;

Leaf color: Adaxial expanding between RHS 138A and RHS 143A and abaxial expanding nearest RHS 138B; mature adaxial nearest RHS 137A and mature abaxial nearest RHS 138A; winter dormant, with no leaves present;

Foliage fragrance: None detected;

Veins: Pinnate; glabrous adaxial and abaxial, midrib about 1.5 mm wide at base; slightly impressed adaxial and costate abaxial;

Vein color: Young adaxial midrib and lateral veins nearest RHS N144A, young abaxial midrib nearest RHS 145C and lateral veins nearest RHS 146D; mature adaxial midrib and lateral veins nearest RHS 146D, mature abaxial midrib nearest RHS 145A and lateral veins nearest RHS 146C;

Petiole: Leaves sessile;

Stems: Cylindrical; stiff; upright; glabrous, limited branching below flowers; to about 58.0 cm long and 10.0 mm diameter near base; anthocyanin pigment heavy distally;

Stem color: Nearest RHS 146B, developing ridges of nearest RHS 161A with maturity;

Nodes: 15 nodes before flowers; average about 3.8 cm apart;

Node color: Color nearest RHS 146B;

Inflorescence: Upright; with 11 branched nodes; flowering in about the upper 34.0 cm and about 20.0 cm wide; average of 500 flowers;

Flowers: Perfect; salverform; mostly flat faced; about 34.0 mm across face and 25.0 mm long; with fused corolla tube about 22.0 mm long and 4.0 mm diameter near face and 2.0 mm diameter at base; attitude upright to outwardly;

Flower longevity: About 5 days on plant; self-cleaning;

Flower fragrance: Lightly sweet;

Buds one to two days prior to opening: Narrowly clavate; bluntly acute apex with rounded base; petals implicate; about 24.0 mm long, 6.0 mm long in terminal bulb portion and 18.0 mm long in corolla tube; corolla tube to 3.5 mm diameter near face and 2.0 mm diameter at base, bulb to 5.0 mm diameter;

Bud color: Exposed petal bulb portion nearest RHS 79C; corolla tube portion nearest RHS 79B; calyx nearest RHS 146C with transparent margins and a moderate blush of nearest RHS 187B;

Petals: Five; consisting of limb and basal claw fused into corolla tube; limb obdeltoid to nearly orbicular; apex rounded, margin entire; limbs imbricate to about 20 percent; glabrous adaxial and abaxial corolla tube puberulent;

Petal size: Limb about 15.0 mm long and 15.0 mm wide near middle; corolla tube about 22.0 mm long and 4.0 mm diameter near face and 2.0 mm diameter near base;

Petal color upon first opening and as maturing:

*Adaxial*.—Limb darker than either RHS 77A or RHS 72A, with lighter halo between RHS N80D and N75D about 1.5 mm from center inner eye distally extending about 1.5 mm, and a central eye and proximal midrib of nearest RHS 77A, proximal 3.0 mm of corolla tube nearest RHS 145D, remaining distal tube portion nearest RHS 79D.

*Abaxial*.—Limb nearest RHS N82B, proximal 3.0 mm of tube nearest RHS 145D, remaining distal tube portion nearest RHS 79B.

Petal color upon drying and before dehiscing:

*Adaxial*.—Limb variable with portions nearest RHS 77A and RHS N88B with a central eye and midrib nearest RHS N78A; proximal 3.0 mm of tube base nearest RHS 145D, remaining distal tube portion nearest RHS 79C.

*Abaxial*.—Limb variable with portions between RHS 77B and RHS N78B and other portions nearest RHS N88B, proximal 3.0 mm, of tube nearest RHS 145C, remaining distal tube portion nearest RHS 79D.

*Androecium*.—Typically five.

Filaments: Typically five, adnate to inner corolla to various heights about 16.0 mm to 20.0 mm from base; free in the distal 0.5 mm to 1.0 mm long and 0.2 mm in diameter; color nearest RHS NN155D;

Anther: Five; oblong elliptic; basifixed; longitudinal; oblong, about 3.0 mm long by 1.0 mm wide; color nearest RHS 11A;

Pollen: Nearly microscopic; color nearest RHS 11D;
Gynoecium: One pistil per flower; 25.0 mm long;
Style: Cylindrical; about 21.0 mm long and 0.3 mm diameter when flower is mature; persistent after flower abscission; color nearest RHS 145C;
Stigma: Trifid in proximal 1.0 mm long, about 0.2 mm diameter; color nearest RHS 1C;
Ovary: Inferior; conical; glabrous; lustrous; slightly acute apex and truncate base; about 3.0 mm long and 1.0 mm diameter; color nearest RHS 143A;
Calyx: Campanulate; about 10.5 mm long and 4.0 mm across at apex;
Sepals: Five; linear; adaxial slightly lustrous and matte abaxial; narrowly acute apex, fused in basal 5.0 mm, free in distal 5.5 mm; margin entire and translucent; individually about 10.5 mm long and 1.0 mm wide at fusion;
Sepal color: Adaxial center nearest RHS 146D proximally and nearest RHS NN137A, margin nearest RHS 155C with strong blush distally in margin and center nearest RHS N187A; abaxial nearest RHS 146B with strong blush to nearly solid nearest RHS N187A and margin variable nearest RHS 155C and RHS 155C strongly blushed with nearest RHS N79B;
Peduncle: Glabrous; stiff; upright; cylindrical; highly branched; to 34.0 cm long and 5.0 mm diameter; with up to 28 branches to about 2.5 mm diameter at base and 25.0 cm long;
Peduncle color: Nearest RHS 187A;
Pedicle: Cylindrical; glabrous; lustrous; flexible; upright to outwardly; to about 4.0 mm long and 1.0 mm diameter;
Pedicle color: Nearest RHS 146C with strong blush of nearest RHS 187A;
Fruit: Rare; dehiscent, few-seeded capsule, typically 1 with up to 3 seeds; fecundity low; ovoid with acute to apiculate apex and rounded to truncate base; glabrous; to about 7.0 mm and 4.0 mm diameter; color at maturity nearest RHS 165B distally and nearest RHS 164B proximally;
Seeds: Flattened ellipsoidal; glabrous; to 4.0 mm long, 1.5 mm across and 1.5 mm thick; color nearest RHS 202A;
Hardiness and culture: The new plant grows best with full sun, light moisture and deep drainage; hardy to at least from USDA zone 3 through 8.
Disease and pest resistance: *Phlox* 'Ultraviolet' demonstrates good powdery mildew (*Erysiphe cichoracearum*) resistance under conditions that would normally show symptoms.

I claim:

1. A new and distinct cultivar of Tall *Phlox, Phlox* plant named 'Ultraviolet', as herein described and illustrated.

* * * * *